(12) United States Patent
Oppenheim et al.

(10) Patent No.: US 10,455,072 B2
(45) Date of Patent: Oct. 22, 2019

(54) SYSTEMS AND METHODS FOR ENABLING OPTICAL TRANSMISSION OF DATA BETWEEN A SENSOR AND A SMART DEVICE

(71) Applicant: LABSTYLE INNOVATION LTD., Caesarea Industrial Park (IL)

(72) Inventors: Dov Oppenheim, Tel-Aviv-Jaffa (IL); Haim Krief, Hadera (IL)

(73) Assignee: LABSTYLE INNOVATION LTD., Caesarea (IL)

( * ) Notice: Subject to any disclaimer, the term of this patent is extended or adjusted under 35 U.S.C. 154(b) by 0 days.

(21) Appl. No.: 15/927,034

(22) Filed: Mar. 20, 2018

(65) Prior Publication Data

US 2018/0270341 A1 Sep. 20, 2018

Related U.S. Application Data

(60) Provisional application No. 62/474,011, filed on Mar. 20, 2017.

(51) Int. Cl.
*H04M 1/725* (2006.01)
*H04M 1/02* (2006.01)
*A61B 5/15* (2006.01)
*A61B 5/151* (2006.01)
*A61B 5/157* (2006.01)
(Continued)

(52) U.S. Cl.
CPC ......... *H04M 1/72527* (2013.01); *A61B 5/157* (2013.01); *A61B 5/150022* (2013.01); *A61B 5/15087* (2013.01); *A61B 5/15186* (2013.01); *A61B 5/150358* (2013.01); *H04M 1/026* (2013.01); *H04M 1/7253* (2013.01); *A61B 5/14532* (2013.01); *G01N 33/92* (2013.01); *H04M 2250/52* (2013.01); *Y02D 70/26* (2018.01)

(58) Field of Classification Search
CPC .................................................. H04B 10/116
See application file for complete search history.

(56) References Cited

U.S. PATENT DOCUMENTS 8,256,673 B1 * 9/2012 Kim ..................... G06K 7/1095
235/437
2006/0222567 A1 * 10/2006 Kloepfer ................ G01N 21/78
422/68.1
(Continued)

*Primary Examiner* — Wen W Huang
(74) *Attorney, Agent, or Firm* — Symbus Law Group, LLC; Clifford D. Hyra

(57) ABSTRACT

A system is herein provided for enabling optical transmission of data between a sensor and a smart device, including a computing device running testing related code in a materials testing Application, wherein the device has a screen and a camera in proximity to the screen; a materials testing adaptor including a light source and a light receiver, wherein the adaptor is adapted to be placed at least partially over the computer device screen, and at least partially over the computer device camera; wherein the computer device communicates data optically to the testing adaptor using at least a part of the screen, and the testing adaptor communicates data optically to the computer device using the light source; and wherein the computer device receives data optically from the testing adaptor using the camera, and the testing adaptor receives data optically from the computer device using the light receiver.

5 Claims, 13 Drawing Sheets

(51) Int. Cl.
G01N 33/92 (2006.01)
A61B 5/145 (2006.01)

(56) References Cited

U.S. PATENT DOCUMENTS

| | | | |
|---|---|---|---|
| 2011/0191059 A1* | 8/2011 | Farrell | A61B 5/14532 |
| | | | 702/130 |
| 2011/0256024 A1* | 10/2011 | Cole | A61B 5/0022 |
| | | | 422/68.1 |
| 2013/0237155 A1* | 9/2013 | Kim | H04W 12/06 |
| | | | 455/41.2 |
| 2013/0267032 A1* | 10/2013 | Tsai | G01N 21/78 |
| | | | 436/95 |
| 2014/0072189 A1* | 3/2014 | Jena | G01N 21/8483 |
| | | | 382/128 |
| 2015/0338387 A1* | 11/2015 | Ehrenkranz | A61B 5/6898 |
| | | | 424/450 |
| 2015/0359458 A1* | 12/2015 | Erickson | G01N 33/52 |
| | | | 455/557 |
| 2016/0080548 A1* | 3/2016 | Erickson | H04M 1/72527 |
| | | | 455/556.1 |
| 2016/0131592 A1* | 5/2016 | Cooper | G01N 21/78 |
| | | | 356/402 |
| 2018/0372714 A1* | 12/2018 | Chen | G01N 27/3273 |

* cited by examiner

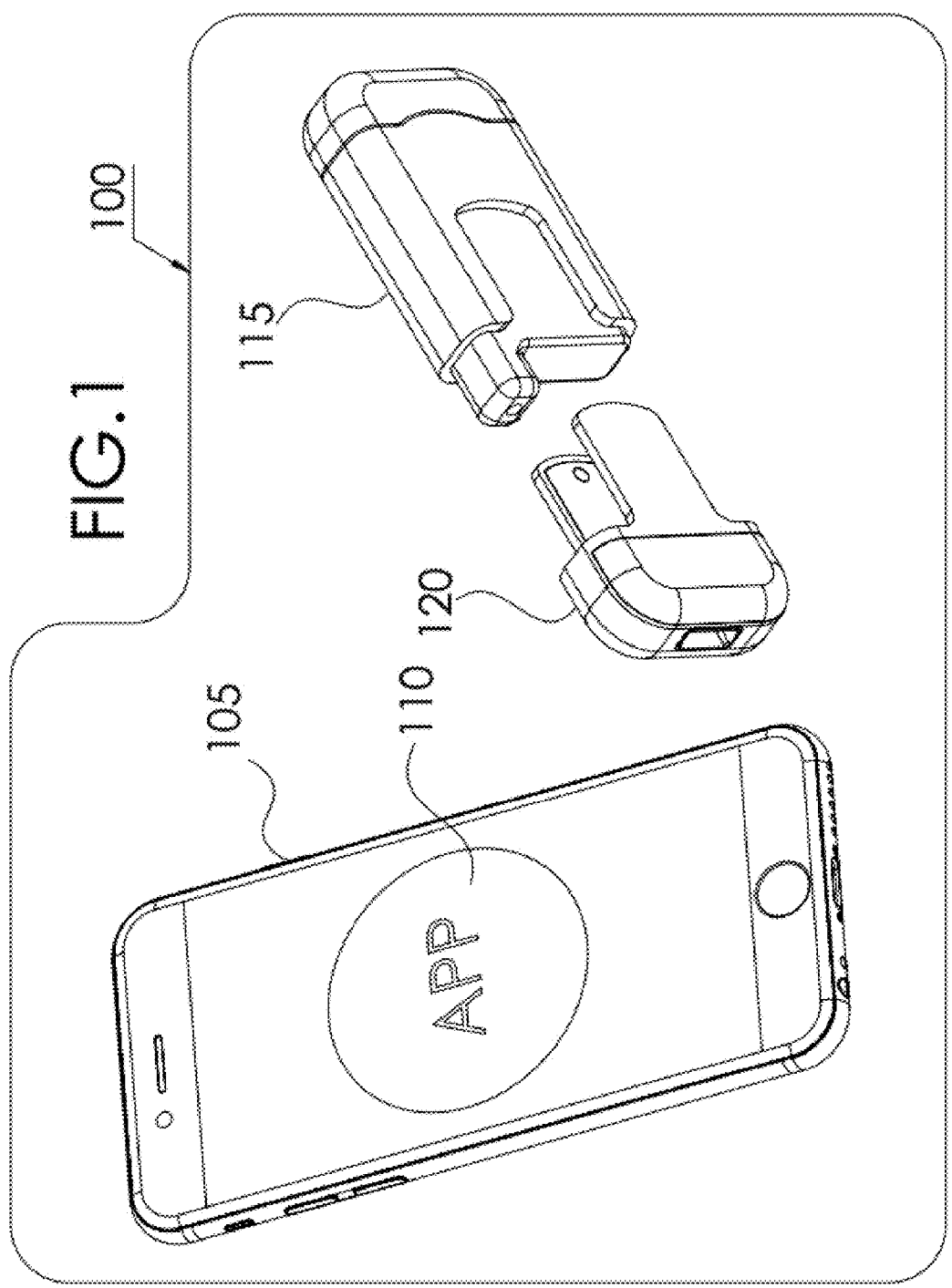

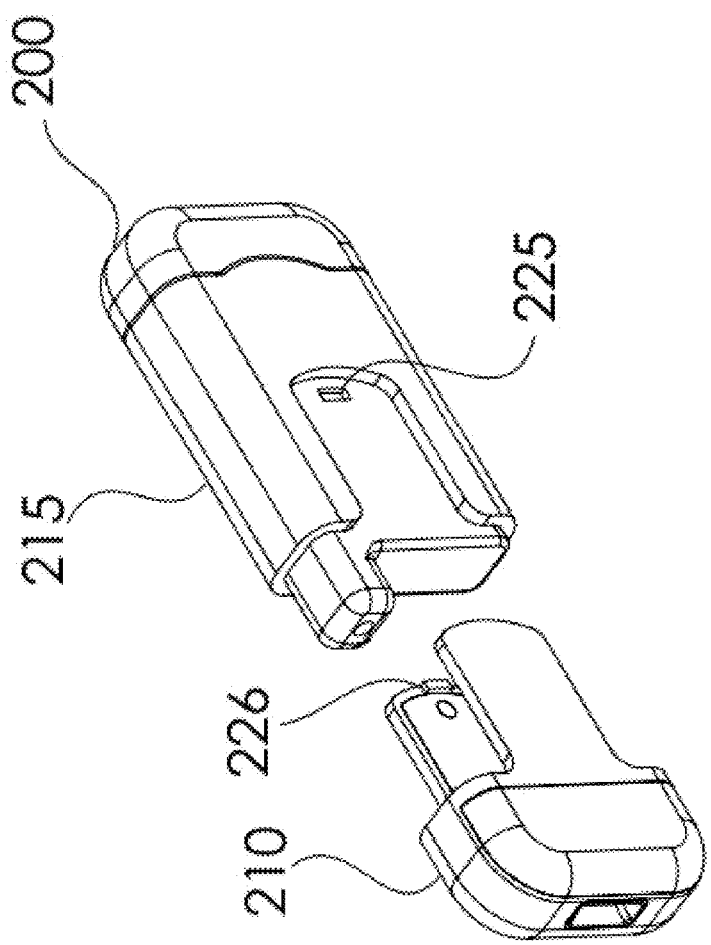
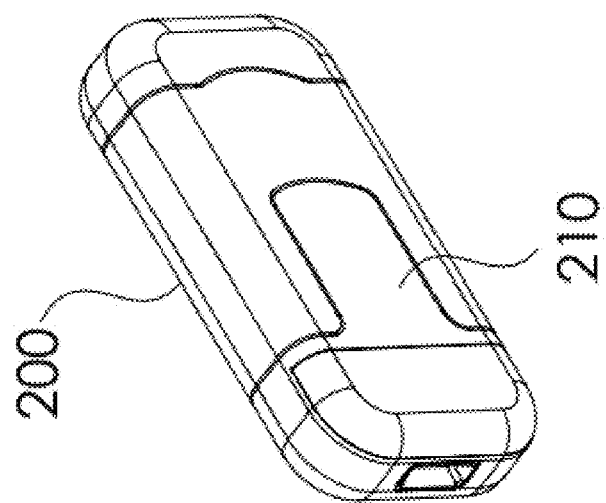

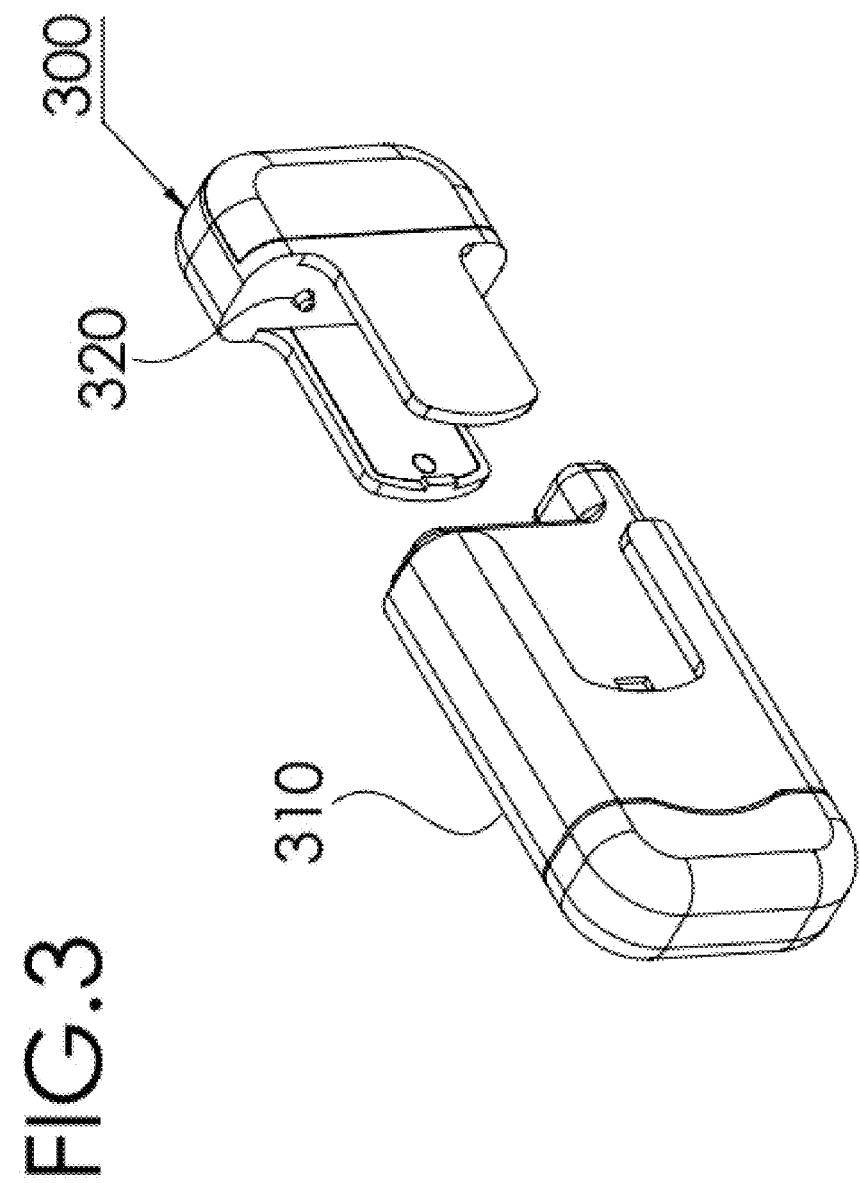

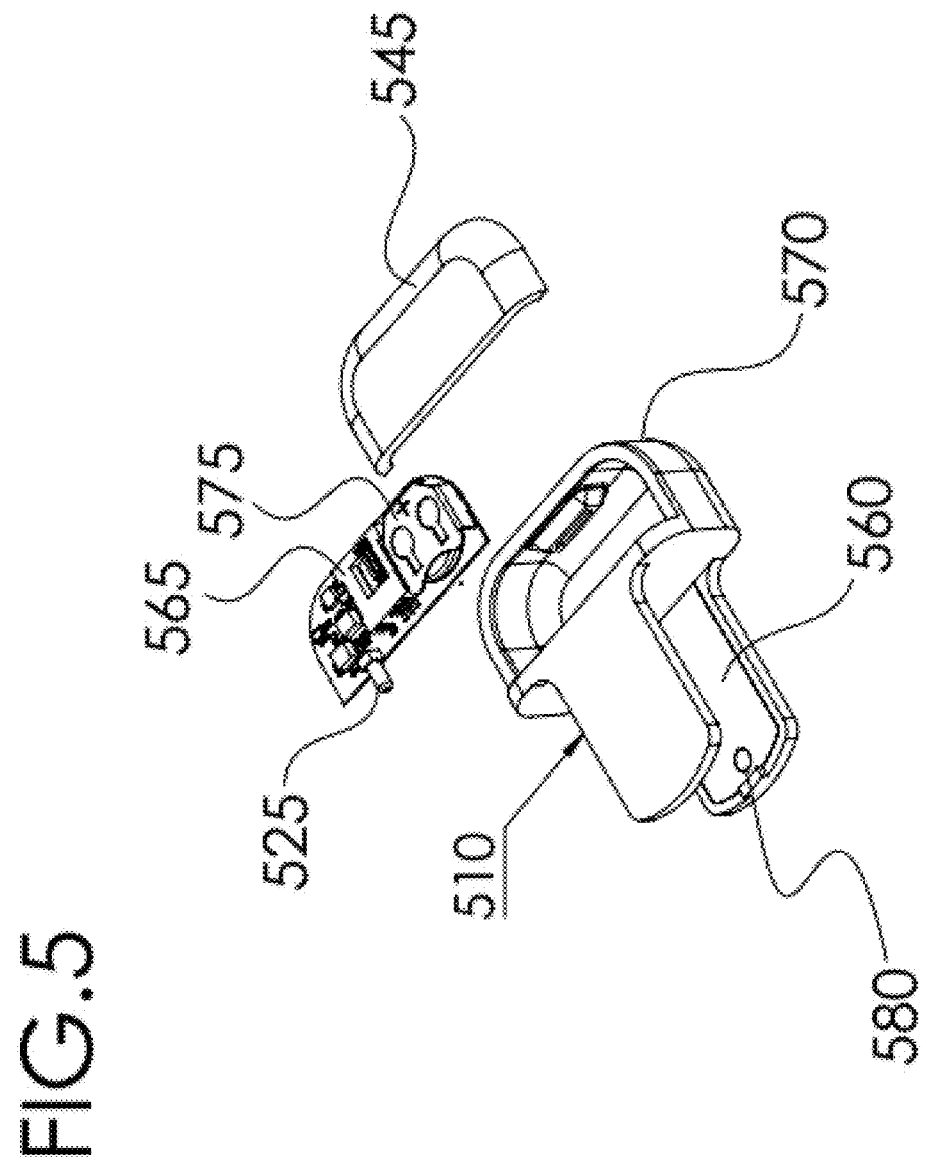

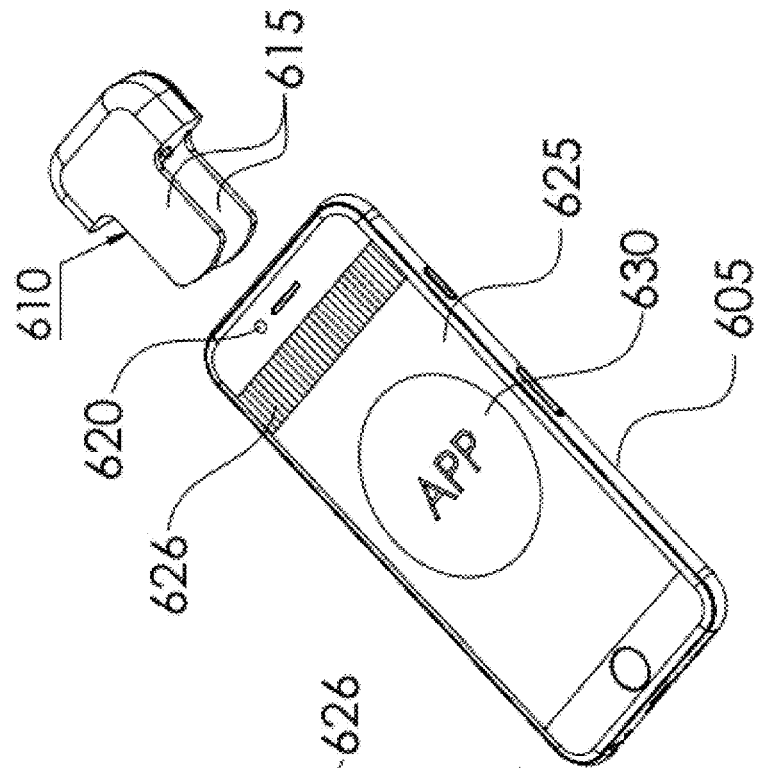
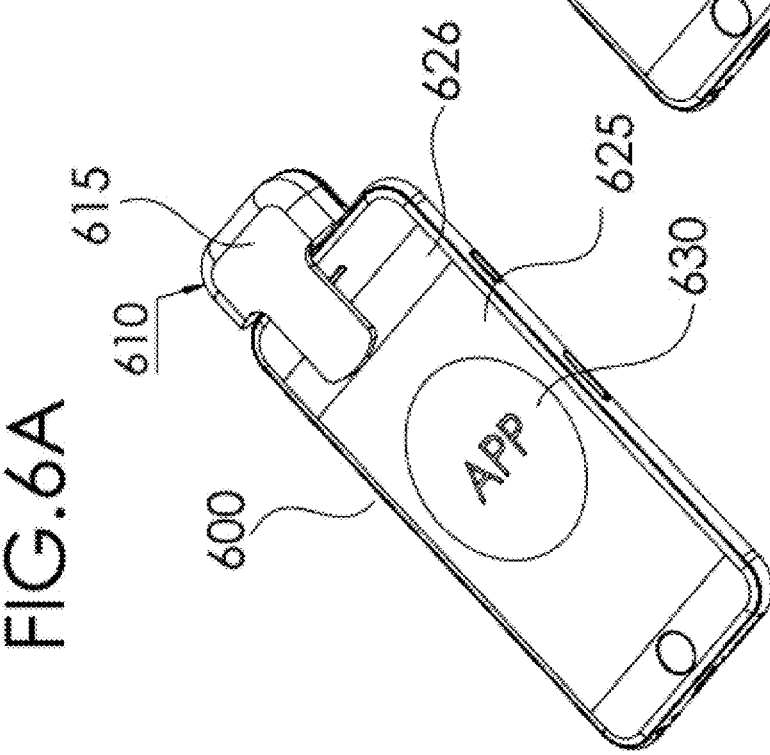

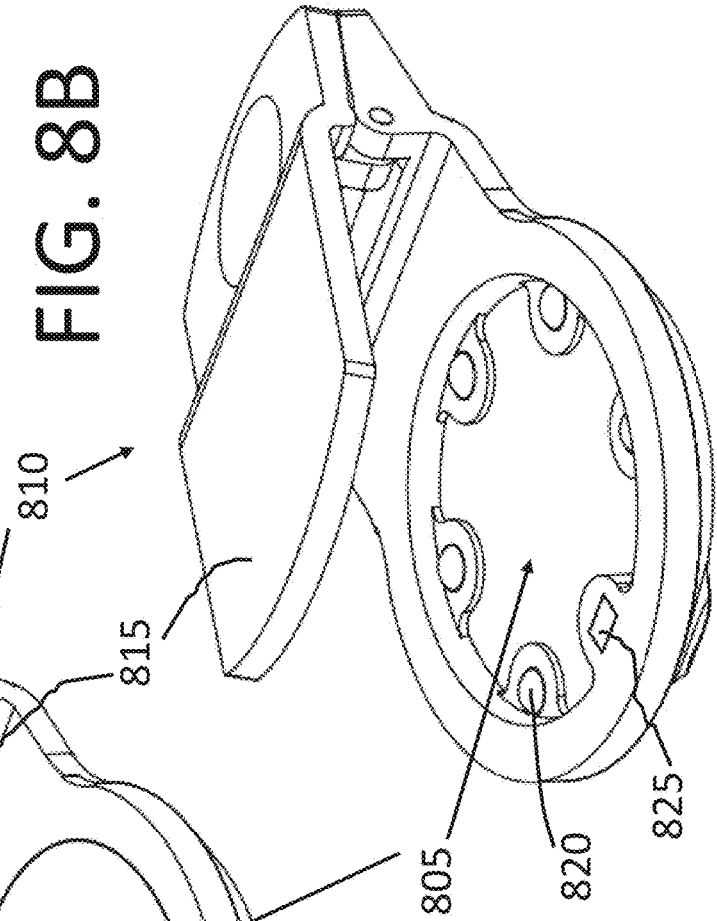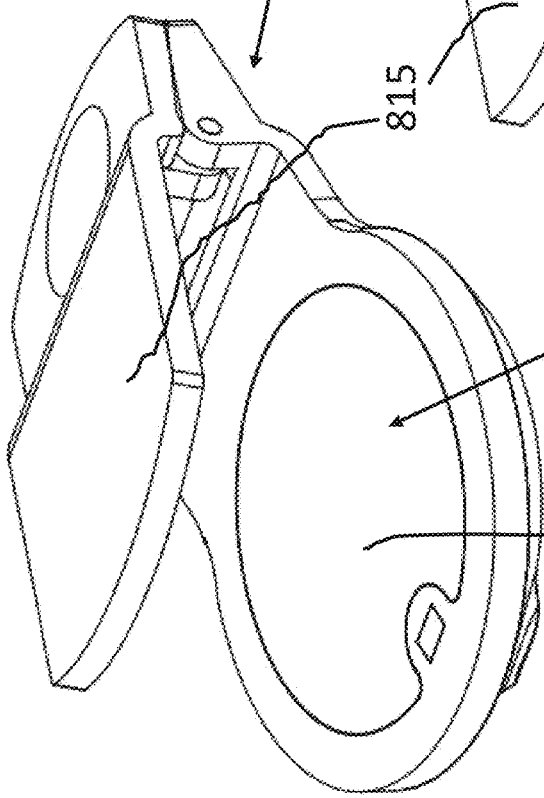

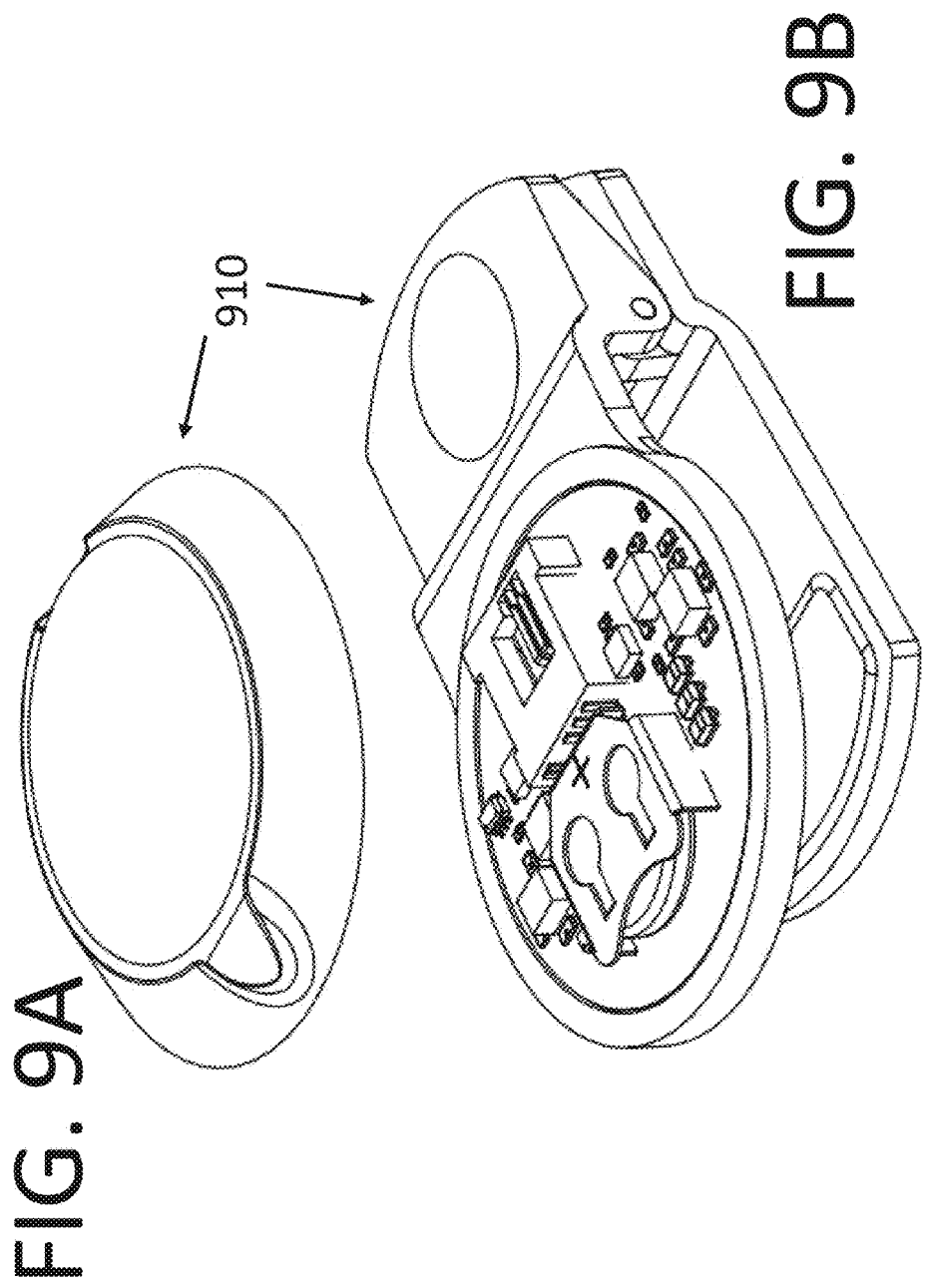

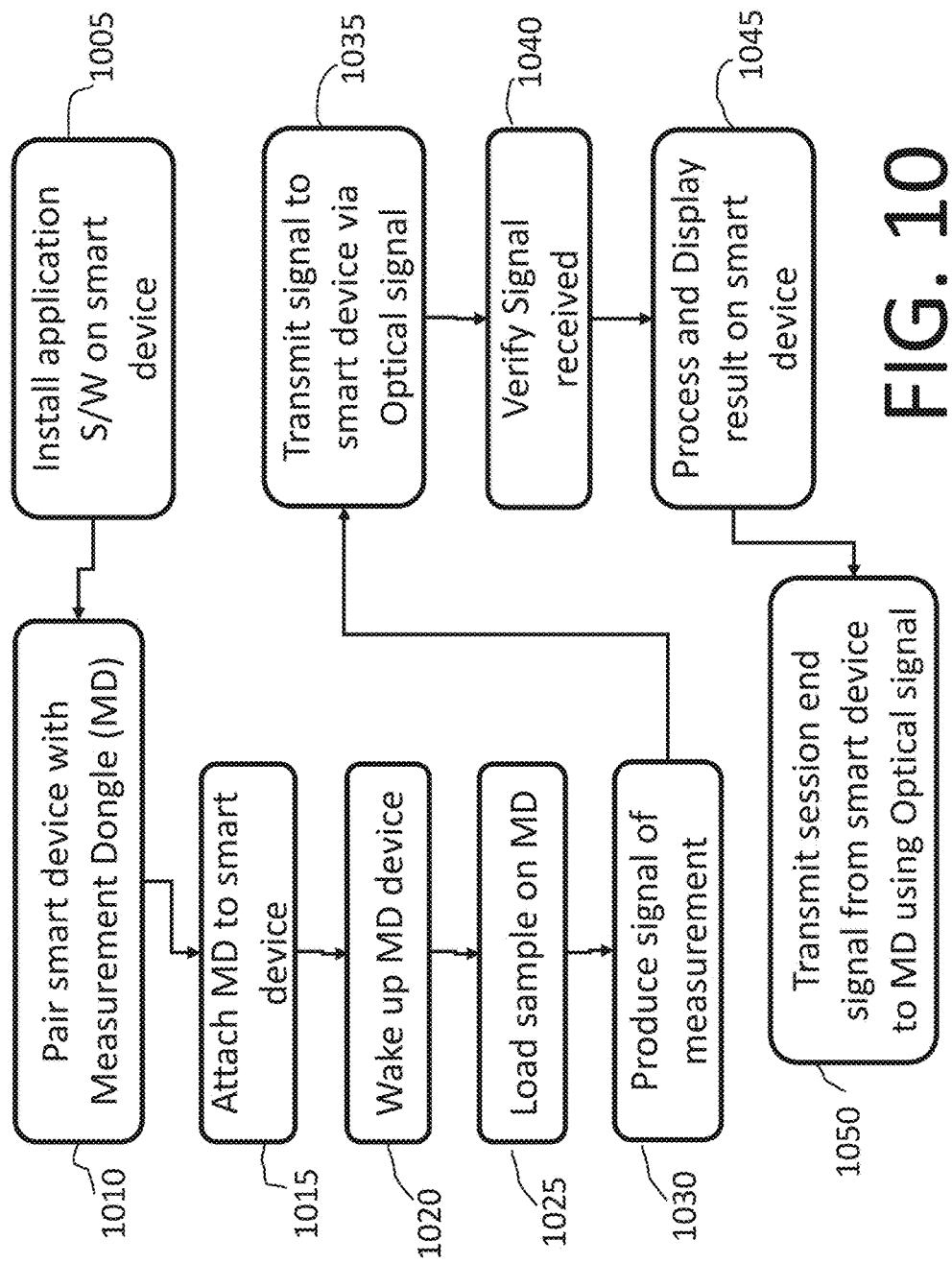

| R | G | B | Color | Signal |
|---|---|---|---|---|
| 0 | 0 | 0 | Off | |
| 0 | 0 | 1 | Blue | "10" |
| 0 | 1 | 0 | Green | "01" |
| 0 | 1 | 1 | Cyan | Idle/stop |
| 1 | 0 | 0 | Red | "00" |
| 1 | 0 | 1 | Magenta | "11" |
| 1 | 1 | 0 | Yellow | Start bit |
| 1 | 1 | 1 | White | |

FIG. 11

SYSTEMS AND METHODS FOR ENABLING OPTICAL TRANSMISSION OF DATA BETWEEN A SENSOR AND A SMART DEVICE

CROSS REFERENCE TO RELATED APPLICATIONS

This application claims priority from U.S. Provisional Patent Application No. 62/474,011, filed 20 Mar. 2017, entitled "SYSTEMS AND METHODS FOR ENABLING OPTICAL TRANSMISSION OF DATA BETWEEN A SENSOR AND A SMART DEVICE", which is incorporated in its entirety herein by reference.

FIELD OF THE INVENTION

In some embodiments, the instant invention is related to methods and systems for connecting between devices, and particularly for connecting a sensor to a camera supported computing device.

BACKGROUND OF THE INVENTION

In recent times, it has become feasible to use smart phones or other mobile devices as sensors, and most devices have multiple sensors built into them. Still there are many sensors that are not integrated into typical smart devices, for example, medical devices or medical wellness tools that require dedicated sensors and/or testers etc. In such cases, there have been many efforts to connect the external sensors to the smart devices, for the smart devices to perform the reading, processing and/or displaying of the sensor data.

Further, with the explosion of device options and types, it is important to make use of a communications or connection technology that facilitates connection between the smart devices and the external sensors, to allow substantially all sensors to connect to substantially all smart devices. For example, a smart phone may be used as a platform for performing various fluid tests, thereby to provide a mass of people worldwide with the opportunity to easily monitor and follow up various physiological parameters including without limitation, glucose levels, cholesterol levels, hemoglobin level etc., without the need to go to the doctor and without the need to go to a laboratory in order to perform such biological tests.

There is a need for a substantially universal connection to be easy to setup, to have reasonable energy demands, and to provide safe and reliable communications.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

FIG. 1 is a graphical illustration of a fluids testing system, with an optical transmission module, according to some embodiments;

FIG. 2A is a graphical illustration of a fluids testing apparatus, with an optical transmission module, in a closed position, wherein a testing module is integrated with a testing device for connecting the testing device optically to a mobile communications or computing device, according to some embodiments;

FIG. 2B is a graphical illustration of a fluids testing apparatus, with an optical transmission module, in an open position, wherein a testing module is integrated with a testing device for connecting the testing module optically to a mobile communications or computing device, according to some embodiments;

FIG. 3 is a graphical illustration of a fluids testing apparatus, with a detached testing device including an optical transmission module, wherein the testing module connects optically to a mobile communications or computing device, when in open mode, according to some embodiments;

FIG. 5 is a fragmented or modular illustration of a fluids testing device for measuring a sample from a test strip, and adapted to communicate test results optically to and from a mobile communications or computing device, according to some embodiments;

FIGS. 6A-6B are graphical illustrations of a fluids testing device for measuring a fluid sample from a test strip, in optical association with a mobile communications or computing device, according to some embodiments;

FIGS. 8A-8B are graphical illustrations of an alternative embodiment of a fluids testing device for measuring a sample from a test strip, showing optical elements in a clip on type optical communications enabled fluids testing device, according to some embodiments;

FIGS. 9A-9B are graphical illustrations of components of an alternative embodiment of an optical communications enabled fluids testing device, for measuring a sample from a test strip, in optical association with a mobile communications or computing device, according to some embodiments;

FIG. 10 is a flow chart showing a process for fluids testing using fluids testing device wirelessly connected to a mobile communications or computing device, according to some embodiments of the present invention;

FIG. 11 is a table showing an example of an algorithm using RGB light to provide signals to a device camera, for enabling fluids testing using a fluids testing device wirelessly connected to a mobile communications or computing device, according to some embodiments of the present invention;

SUMMARY

Figure 4:
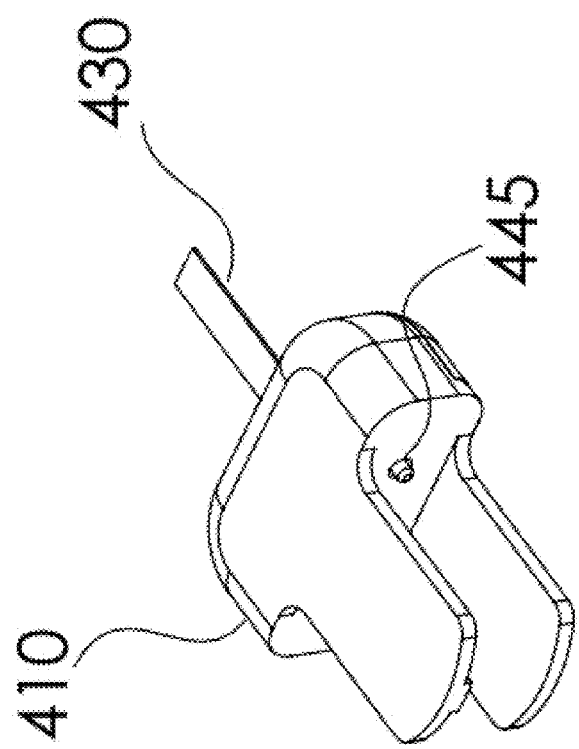
FIG. 4 is a graphical illustration of a fluids testing device for measuring a sample from a test strip, and adapted to communicate test results optically to a mobile communications or computing device, according to some embodiments.

In some embodiments of the present invention, a method for measurement testing using an optical communications adaptor device is provided, for enabling optical connection of a testing apparatus to a communications device.

In some embodiments, a system for enabling optical transmission of data between a sensor and a smart device is provided, including a computing device running testing related code in a materials testing Application, wherein the device has a screen and a camera in proximity to the screen; a materials testing adaptor including a light source and a light receiver, wherein the adaptor is adapted to be placed at least partially over the computer device screen, and at least partially over the computer device camera; wherein the computer device communicates data optically to the testing adaptor using at least a part of the screen, and the testing adaptor communicates data optically to the computer device using the light source; and wherein the computer device receives data optically from the testing adaptor using the camera, and the testing adaptor receives data optically from the computer device using the light receiver.

In some embodiments, the testing adaptor is attachable to a testing apparatus, wherein when attached, the power source for the testing adaptor is passive, whereas when the testing adaptor is detached from the testing apparatus, the power source for the testing adaptor is active.

In some embodiments, a liquid measurement testing apparatus is provided, that includes an optical dongle to connect a measurement device to a smart device, using one or more LEDs on the measurement device to transmit data to a camera on the smart device, and using a light sensor on the measurement device to receive data from the smart device screen.

In some embodiments, a method for fluid measurement testing using a communications adaptor device, is provided, for enabling optical communications between a measurement device and a smart device.

DETAILED DESCRIPTION OF THE INVENTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples are given in connection with the various embodiments of the invention, which are intended to be illustrative, and not restrictive.

The present invention, in some embodiments, describes a substantially universal data connection between an external sensor or tester and a smart device, in particular a camera supported device, in a way that is easy to setup, has low energy demands, does not rely on cables of ports for connection, and provides safe and reliable communications.

The present invention, in further embodiments, describes a novel fluid testing apparatus for performing a parameter measurement in a fluid sample including a strip adapted to absorb a fluid sample and to produce a signal indicative of the parameter level in the sample; and a testing device adapted to optically connect the fluid testing apparatus to a mobile computing or communications device, to thereby allow delivery of the produced signal or a correlated signal to the mobile computing or communications device for obtaining a measurement of the fluid parameter being measured.

Further embodiments of the present invention are aimed to provide a blood testing apparatus, and in particular, for performing glucose measurement in a blood sample, that is communicated optically to a smart device for display of the results.

Embodiments of the present invention further provide a blood glucose monitoring apparatus or kit for determining glucose level in a blood sample of a user comprising: a sensor measurement device adapted to with a slot adapted to allow collection of a blood sample: a glucose strip adapted to absorb the blood sample and to produce a signal indicative of the glucose level in the sample, when connected to the measurement device; an optical data transfer (ODT) module to optically connect the glucose strip to a communications or computing device, such as a camera supported smart phone.

Embodiment s of the present invention are further aimed to provide a mobile miniature laboratory system capable of performing fluid parameter measurement of a sample, the system comprising: A smart phone or device installed with a dedicated application software; A strip adapted to absorb a fluid sample and to produce a signal indicative of the parameter level in the sample; A testing device; An optical adaptor adapted to connect the strip optically to a smart phone to thereby allow delivery of the produced signal or a correlated signal to the smart phone or device for obtaining a measurement of the fluid parameter displayed on the smart phone or device.

In accordance with embodiments of the present invention the testing apparatus provided herein may be used to perform various fluid tests such as, for example, toxicity tests, and various biological tests produced from physiological fluids such as blood, urine, amniotic fluid, or saliva, such as glucose level, cholesterol level, coagulation test, pregnancy test (in blood or urine). HIV test, PH test, fetal lung maturation test, and more. The apparatus in some cases may be a small size fully disposable apparatus. The apparatus in some cases may be made of one unit or more. The apparatus may be optically connected to a smart phone or other smart device, and may rely on the smart device for display means, storage and communications for operation.

The testing device provided herein is connectable to a smart device in a complementary manner, as the combination of the two together with specific software installed on the smart device provides a novel system capable of performing various physiological fluids tests in a user friendly, fully disposable, and inexpensive manner. In addition, the apparatus may communicate optically with any smart device with a camera and computing power such as a media device, iPad or tablet, wearable computer, smart watch, notebook or desktop computer, or any non-mobile computers.

In accordance with features of the invention, for testing a blood sample the apparatus may comprise the general following components: a lancing device to sample blood from a finger, forearm or palm of a user; an electrochemical strip, such as a glucose strip or a cholesterol strip adapted to collect blood sample and to produce data; and an electrical circuit that is functionally adapted to receive the data produced by said electrochemical strip and translate the chemical results into an electronic signal (analog or digital) that is, preferably, transmitted to a smart device, by optical transmission.

For testing a urine sample, saliva sample or amniotic fluid sample the apparatus may comprise an electrochemical or chemical strip adapted to absorb the liquid sample and to produce data, and an electric circuit that is functionally adapted to receive the data produced by said electrochemical or chemical strip and translate the chemical results into an electronic signal (analog or digital) that is preferably, transmitted optically to a smart phone. The electrochemical or chemical strip could be test-specific strips (for example glucose strip, cholesterol strip, pregnancy strip, protein strip, etc.)

In accordance with one feature of the present invention, a fluid testing apparatus for performing parameter measurement in a fluid sample is provided. The apparatus comprises: a strip adapted to absorb a fluid sample and to produce a signal indicative of the parameter level in the sample; and an adaptor adapted to optically connect the strip to a smart device to thereby allow delivery of the produced signal or a correlated signal to the smart phone for obtaining a measurement of the fluid parameter displayed on the smart phone, wherein the testing apparatus relies on the smart device at least for display means. The produced signal or a correlated signal may be processed at least partially by the fluid testing apparatus before delivery to the smart phone. Alternatively, the produced signal or a correlated signal may be delivered to the smart phone for processing by a dedicated application software installed on the smart device. Upon delivery of the signal or a correlated signal to the smart device, processing of the signal is performed by dedicated application software installed on the smart device, and a measurement is being displayed on the smart device. In accordance with a further variation of the invention, the apparatus further relies on the smart device for storage of data and communication. The measured parameter in accordance with variation of the invention may be a toxic substance.

The fluid sample may also be a physiological fluid, such as a blood sample, a urine sample, an amniotic fluid sample, and a saliva sample, or a mixture thereof. In such variation, the measured parameter may be for example, a glucose level, cholesterol level, HbA1C level, Hemoglobin level, fetal lung maturation level, and PSA level. In a specific variation of the invention, the apparatus is adapted to perform blood tests and comprises at least two separable subunits, first subunit comprises at least: a lancing device and housing; and second subunit comprises at least: a slot adapted to allow collection of the physiological fluid sample, a strip, an adaptor to thereby allow physical attachment and signals transmission between the testing apparatus and the smart device, and housing. In such variation, the apparatus may further comprise a thread that functionally allows a user to adapt the lancet length to his/her physical dimensions.

The present invention further provides a physiological fluid testing apparatus for performing a parameter measurement in a fluid sample comprising: A strip adapted to absorb a physiological fluid sample and to produce a signal indicative of the parameter level in the sample. An adaptor adapted to optically connect the strip to a smart device to thereby allow deliver) of the produced signal or a correlated signal to the smart device for obtaining a measurement of the fluid parameter displayed on the smart device, wherein the physiological fluid testing apparatus relies on the smart device at least for display means. The produced signal or a correlated signal may be processed at least partially by the testing apparatus before delivery to the smart device. Alternatively, the produced signal or a correlated signal may be delivered optically to the smart device for processing by dedicated application software installed on the smart device. The fluid sample in such variation may be either one of a blood sample, a urine sample, an amniotic fluid sample, a saliva sample, or a mixture thereof, and wherein, said measured parameter is either one of a glucose level, cholesterol level. HbA1C level, Hemoglobin level, fetal lung maturation level, and PSA level. The apparatus is preferably fully disposable. In accordance with one another variation the apparatus may be connected and rely on a tablet device or another mobile, portable or wearable device, and/or a smart phone.

In one further variation of the invention, a blood testing apparatus for performing glucose measurement in a blood sample is provided. The apparatus comprising: A glucose strip adapted to absorb a blood sample and to produce a signal indicative of the glucose level in the blood sample; and an adaptor adapted to optically connect the glucose strip to a smart device to thereby allow delivery of the produced signal or a correlated signal to the smart device for obtaining a measurement of the glucose level displayed on the smart device, wherein the blood testing apparatus relies on the smart device at least for a display means. In such variation, the produced signal or a correlated signal may be processed at least partially by the blood testing apparatus before delivery to the smart device. Alternatively, the produced signal or a correlated signal is delivered to the smart device for processing by a dedicated application software installed on the smart device. Processing may be conducted by reading the peak and timing of peak of a current or a voltage signal obtained upon loading the blood sample on the glucose strip. In such variation, the apparatus is preferably fully disposable. In accordance with one another variation the apparatus may be connected and rely on a tablet device or another mobile, portable or wearable device, and/or to a smart phone.

Embodiments of the present invention may be further directed to a method for performing a fluid parameter measurement in a fluid sample comprising the steps of: Installing a dedicated application software on a smart phone; Loading a fluid sample on a fluid testing apparatus, the apparatus comprising: a strip adapted to absorb such sample and to produce a signal indicative of the parameter level in the sample; and an adaptor adapted to optically connect the strip to a smart phone to thereby allow delivery of the produced signal or a correlated signal to the smart phone for obtaining a measurement of the fluid parameter displayed on the smart phone, wherein the testing apparatus relies on the smart phone at least for display means; initiating an optical connection between the testing apparatus and the smart phone to thereby allow wireless communication between the apparatus and the smart phone and optionally delivery of power supply; and obtaining the measured parameter level displayed on the smart phone screen. Alternatively, the apparatus may be connected and rely on a tablet device (such as iPad) or an iPod instead of a smart phone. In accordance with one specific variation, the tested fluid is a physiological fluid, such as blood, urine, an amniotic fluid, saliva, or a mixture thereof. The measured parameter may be for example, a glucose level, cholesterol level, HbA1C level, Hemoglobin level, fetal lung maturation level, and PSA level. The strip may be either one of a chemical strip or an electrochemical strip, and the signal transferred to the smart phone may be either an electric current signal or a voltage signal. The produced signal or correlated signal may be processed at least partially by the fluid testing apparatus before delivery to the smart phone. Alternatively, the produced signal or a correlated signal may be delivered to the smart phone for processing by a dedicated application software installed on the smart phone. In one specific variation, processing is conducted by reading the peak and timing of peak of a current of a voltage signal obtained upon loading the fluid sample on the strip.

Embodiments of the present invention further provide a method for performing glucose measurement in a blood sample comprising the steps of: Installing dedicated application software on a smart device; Loading a blood sample on a glucose measurement apparatus, the apparatus comprising: a strip adapted to absorb blood sample and to produce a signal indicative of the glucose level in the sample; and an adaptor adapted to optically connect the strip to a smart phone to thereby allow delivery of the produced signal or a correlated signal to the smart phone for obtaining a measurement of the glucose level displayed on the smart phone, wherein the glucose measurement apparatus relies on the smart phone for display means; connecting the loaded glucose measuring apparatus wirelessly to the a smart phone to thereby allow communication between the apparatus and the smart phone; and obtaining the measured glucose level displayed on the smart phone screen. The apparatus is optionally disposable. In accordance with one another variation the apparatus may be connected and rely on a tablet device or another mobile, portable or wearable device, in addition to a smart phone.

Embodiments of the present invention are further directed to a blood glucose monitoring apparatus for determining glucose level in a blood sample of a user comprising: a lancing device adapted to allow the user obtaining a blood sample; a slot adapted to allow collection of the blood sample: a glucose strip adapted to absorb the blood sample and to produce a signal indicative of the glucose level in the sample; and an adaptor adapted to optically connect the glucose strip to a smart phone via one or more optical communications protocols, to functionally deliver to the smart phone the produced signal or a correlated signal thereof.

The invention is also directed to a mobile hand held, miniature laboratory system capable of performing fluid parameter measurement of a sample, the system comprising: a smart phone installed with dedicated application software; a strip adapted to absorb a fluid sample and to produce a signal indicative of the parameter level in the sample; and an adaptor adapted to optically connect the strip to a smart phone to thereby allow delivery of the produced signal or a correlated signal to the smart phone for obtaining a measurement of said fluid parameter displayed on the smart phone, wherein the testing apparatus relies on the smart phone at least for display means. In a specific variation, the fluid sample may be a physiological fluid sample such as, a blood sample, a urine sample, an amniotic fluid sample, a saliva sample, or a mixture thereof, and wherein, the measured parameter is either one of a glucose level, cholesterol level, HbA1C level, Hemoglobin level, fetal lung maturation level, and PSA level.

In some embodiments, the system of the present invention is configured to utilize cloud-based software, allowing a user to record, save, track, analyze, manage, share, or any combination thereof, all or a portion of the user's diabetes-related information in one lifestyle management platform.

In some embodiments, the apparatus of the present invention periodically synchronizes each user's, of a plurality of users, data in to one place, so a user can maintain control of the user's health. In some embodiments, the user's data is synchronized at selected time intervals, for example, about every second, about every minute, about every hour, about every day, about every week, about every month, about every year, etc. In further embodiments, the synchronization is manual and/or automatic. In some embodiments, the user can initiate synchronization. In an embodiment, the apparatus of the present invention is an all-in-one mobile and cloud based diabetes management platform, with glucose measurement device, data capture and analysis, sharing, and social features designed to fit patients with diabetes everyday life.

FIG. 1 is a graphical illustration of a materials testing system, according to some embodiments. As can be seen, fluids testing system 100 includes a computing and/or communications device, for example a smart phone, phablet, tablet or wearable computer or communications device 105, hereinafter referred to as smart phone or more generically as a smart device. Smart device 105 typically includes testing related software, code, algorithms or programs, referred to hereinafter as an Application 110. In general, smart device 105 has an optical transmission module, to send and receive data optically to and from (bi-directional) a mobile communications or computing device. Materials testing system 100 may optionally include a materials testing apparatus 115. Apparatus 115 may be a simple holding a device, or may include other components for supporting user usage or compliance. For example, for blood glucose testing support, apparatus 115 may include testing strips, a lancing mechanism, a strip measurement apparatus etc. Materials testing system 100 further includes a materials testing dongle, adaptor or device 120, which may or may not be detachable from apparatus 115. Testing dongle 120 may include a measurement strip measurement module, as well an in integrated communications module, adapted to transmit measurement results and optionally other data optically to external devices or communications receivers. In some embodiments, a mechanical switch may be used to wake up the communications chip after extraction of the testing device from the testing apparatus. In some embodiments, apparatus 115 may have a casing that is adapted to support power management, for example, by turning on power in the testing dongle 120, when removing from casing of testing apparatus 115.

According to some embodiments, testing dongle 120 may include a communications module that may use a variety of optical and/or wireless communications tools and protocols that may be receivable by smart device 105. For example, testing device 120 may include optical and/or wireless communications means.

In some embodiments, testing device may include a kit of elements for conducting selected tests. For example, testing device may include a cartridge for holding test strips and a lancing device etc.

FIG. 2A is a graphical illustration of a materials testing apparatus 200, with an optical testing device (not seen in figure), in a closed position, wherein testing dongle 210 is integrated with testing apparatus 200 for connecting to a mobile communications or computing device, according to some embodiments. When the materials testing apparatus is in a closed position, as can be seen in FIG. 2A, the optical transmission module is generally in sleep or dead mode, so as not to use substantial power. As can be seen, attachment/ detachment mechanism, for example snap on-snap off spring mechanism, including parts 225 and 226 may be used to fully or partially release the materials testing dongle 210. Of course, other release mechanisms may be used.

FIG. 2B is a graphical illustration of an example of a materials testing apparatus 200, with an optical testing dongle 210, in an open position, wherein a testing dongle 210 is initially integrated with testing apparatus 200, yet can be separated for connecting optically to a mobile communications or computing device, according to some embodiments. When the materials testing apparatus is in an open position, as can be seen in FIG. 2B, the optical testing dongle 210 is optionally changed into wakeup or active mode, so as to be able to optically communicate with the smart device, thereby using power to communicate with the smart device on a selective and limited basis, thereby use relatively minimal power in communicating with the smart device.

FIG. 3 is a graphical illustration of a materials testing apparatus 300, with a detached testing dongle 310 including an optical transmission module (not shown in detail), wherein the transmission module connects optically to a mobile communications or computing device, when in open mode, according to some embodiments. As can be seen, a releasing slider or other releasing mechanism may be used to release the materials testing dongle 310. As can be seen further, materials testing apparatus 300 may include a circuit breaker or switch, for example a magnet 320, for closing and thereby waking up the power circuit on dongle 310, when closed, for example, when the testing dongle 310 is detached. As can be seen further, testing dongle 310 may include other or additional circuit breakers and/or or switches for closing and thereby waking up the power circuit of dongle 310 when released or opened, for example, when the testing dongle 310 is detached. For example, the power circuit on dongle 310 may be in a "normally open" or non-operative position, thereby draining zero or minimal energy from the device power source, and when the dongle 310 is detached, this may close one or more switches thereby waking up the power circuit on apparatus 300 and/or dongle 310, and allowing the optics transmission module to enter active mode. In some embodiments, a magnet may be used for the switch.

FIG. 4 is a graphical illustration of a fluids testing dongle 410 for measuring a sample from a test strip, and adapted to communicate test results optically to a mobile communications or computing device, according to some embodiments. As can be seen, testing dongle 410 may further include a circuit breaker or switch, for example switch 445, for closing and thereby waking up the power circuit of dongle 410 when released or opened, for example, when the testing dongle 410 is detached from testing apparatus 400. As can be seen, testing dongle 410 may further include a strip insertion slot (not shown in figure), for receiving test or check strip 430, for example, blood glucose strip, or other strips.

FIG. 5 is a fragmented or modular illustration of an example of a materials testing dongle for measuring a sample from a test strip, and adapted to communicate test results optically to a mobile communications or computing device, according to some embodiments. As can be seen, testing dongle 510 may include a strip socket 565, battery cover 545, covering battery or power source 575, to power the circuit, when the battery is in connected mode, which is generally inside housing 570. Testing dongle 510 may further include a circuit breaker or switch 525 for closing and thereby waking up the power circuit of dongle 510 when released or opened, for example, when the testing dongle 510 is detached from testing apparatus 305. Testing dongle 510 may further include a main PCB, that may support one or more optical elements 560, for example, LEDs, light guides, illuminating plates etc., and light sensor 580.

According to some embodiments, power source, such as a battery 575 in the testing dongle 510 is a long-lasting power supplier, which may be enabled by keeping dongle 510 normally in sleep or dead mode, which changes to active mode only when a mechanical switch is pushed or closed, for example, due to the testing dongle being partly or wholly removed from the testing apparatus.

In some embodiments, a method for wireless diagnostic processing and/or communications is provided for an optical measurement device, comprising: removing of the testing device from a testing apparatus, mechanically waking up a device optical communications module, connecting optically to a smart device, optionally waking up a testing application on the smart device, communication testing results between the testing device and smart device, processing test results on the smart device, displaying test results on the smart device, and following returning of the testing device to the testing apparatus, switching off the testing device to save energy until the next wakeup.

According to some embodiments, a testing process may be initiated fundamentally in a single step, following insertion of a test strip into a testing device into the testing device, since this step may trigger wake up of the testing device communications and/or processing circuitry, that in turn may wake up the smart device via an optical signal, to further process and display the test results on the smart device, without the testing device physically touching the smart device.

In some embodiments, a testing apparatus may connect optically to a wearable communications or computing device, such as a smart watch.

In some embodiments, test results processed on a smart device, smart phone or wearable device may be communicated to a communications cloud, and thereby used to send the data to multiple devices optionally managed by multiple people.

According to some embodiments, testing device and/or testing apparatus may be charged optically, using an optical charging means, to charge or boost the charge or power on the testing device and/or testing apparatus.

FIGS. 6A-6B are graphical illustrations of a fluids testing dongle 610 for measuring a sample from a test strip, in optical association with a mobile communications or computing device 600 or 605, according to some embodiments. As can be seen Sensor Measuring dongle 610 includes a clip like or spring type connection mechanism 615, designed to connect Sensor Measuring dongle 610 onto a smart device, such as a smart phone 605 with a camera. Moreover, the Sensor Measuring Device 610 is designed to enable positioning on the smart device so as to cover the front camera 620 of the smart device and at least a portion of the device screen, for example, at least a part of screen section 626. This positioning is configured to enable the Sensor Measuring dongle 610 to form a communications circuit, both to send optical signals to the smart device, which may be received by the smart device camera 620, and to receive optical signals from the screen 625, and more specifically, from screen optical signaling area 626 of the smart device, for transmitting optical signals to the sensor measuring dongle 610. In some embodiments, the attachment of Sensor Measuring dongle 610 may wake up a power circuit or source in Sensor Measuring dongle 610. In some embodiments, the attachment of Sensor Measuring dongle 610 may wake up the installed application 630 on the smart device. In some embodiments, the attachment of Sensor Measuring Device 610 may turn the smart device camera 620 on, preferably into video capture mode. In some embodiments, a proximity sensor integrated into smart device may enable recognition of the attachment of measuring dongle 610, thereby initiating an optic handshake using the combination of the proximity sensor and the smart device camera.

Figure 7A:
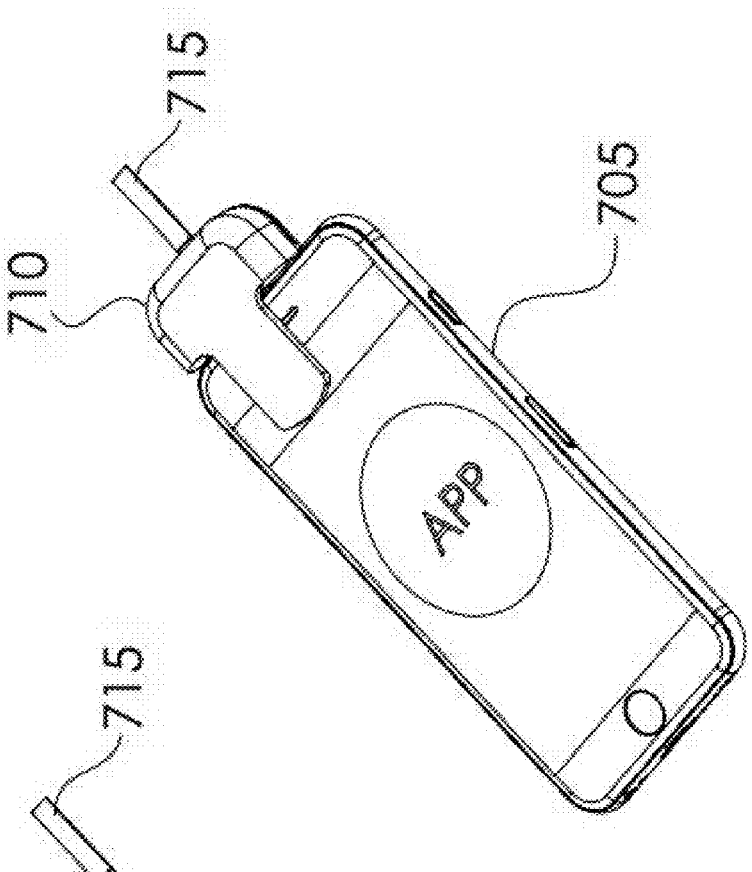
FIGS. 7A-7B are graphical illustrations of a fluids testing device for measuring a sample from a test strip, showing the test strip before and after coupling, in optical association with a mobile communications or computing device, according to some embodiments.
Figure 7B:
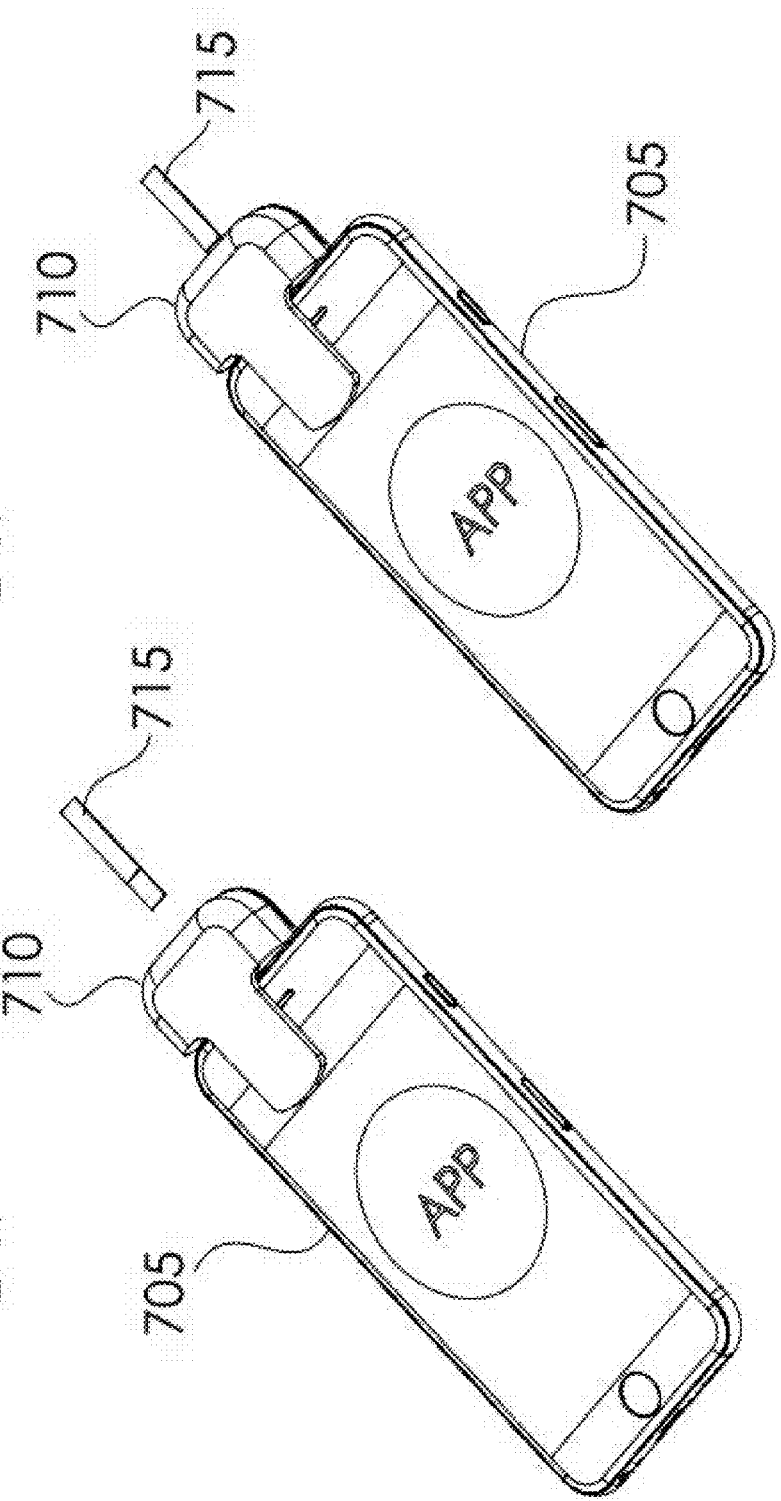

FIGS. 7A-7B are graphical illustrations of a fluids testing dongle 710 for measuring a sample from a test strip 715, in optical association with a mobile communications or computing device 705, according to some embodiments. As can be seen, FIG. 7A shows a measurement dongle 710 clipped on, placed on, or otherwise coupled to, a smart device 705, with a not-yet-engaged sensor stick 715, while FIG. 7B shows a measurement dongle 710 coupled to a smart device 705, with an engaged sensor stick 715.

In some embodiments, following the device handshake, the smart device may provide usage guidelines or instructions to a user, to appropriately operate the smart device, sensor(s), and/or the measurement device. For example, the application running on the smart device may provide instructions including when to enter a sensor or strip, show progress in measurement processing, showing measurement results, data result usage options, and confirmation of data communications stages, etc.

FIGS. 8A-8B are graphical illustrations of an alternative embodiment of a fluids testing dongle for measuring a sample from a test strip, showing optical elements in a clip on type optical communications enabled fluids testing dongle, according to some embodiments. As can be seen, Sensor Measuring dongle 810, shown in upside down position to show the screen side clip 816 optics components 805 in a clear way, includes a sensor receiver or slot (not seen in the figure), clip on mechanism 815, and an optics communication module 805, that may include both one or more optical lamination elements 820, and one or more optic or light sensor(s) 825. For example, the optics communication module 805 may include multiple optics illumination elements 820, for example, LEDs, light guides, or self-illumination surface etc., to provide a diffused lighting effect to transmit data via optic signals. The optics communication module 805 may further include one or more optic sensors or light sensor(s) 825, to receive light signals from the smart device screen, or more particularly from the screen optical signaling area 626 of the smart device or other light emitting source(s). As can be seen in FIG. 8, optical components 835 may be positioned to scatter the light thereby enabling light to be adequately transmitted to the smart device camera, even if the camera is not directly beneath optics communication module 835.

As can be seen, diffusing cover 815 is designed to illuminate in a substantially even distribution or spread effect, to transmit data in optical in an optic protocol to the front camera of the smart device (direction 1), substantially wherever the measurement device may be placed in proximity to the camera. Further photo electric sensor (small window at edge of device #) may be configured to receive light or signals transmitted from the screen (direction 2), for example, to close the communication loop between the devices.

In some embodiments the smart device may include substantially any device with a screen and a camera, for example, providing a method for bi-directional communications between an external sensor or measuring device, and a smart phone, tablet, laptop, desktop computer, wearable computer or communications device etc.

In some embodiments, Bi-directional communication between the measurement device and the smart device, using an optical communications protocol. In some examples, one or more LED lights may be used to transmit signals representing data to be transmitted to the smart device. In further embodiments, the LEDs used may have multiple colored LEDs, for example, RGB LEDs wherein 3 diodes in 1 LED lens can produce a multitude of color flashes, that may enable greater amounts of data to be transmitted between the devices, thereby allowing faster communications. In some embodiments, super bright LEDs may be used with very low current, to produce effective light using low power. The RGB data communications protocol may include, for example, one or more special control signals, Image processing algorithms as described below.

In some embodiments, optical communications module may include a power source, generally in sleep mode, and when in wake-up mode, to enable transmitting power to one or more LED lights and/or optical sensors to enabling the power source to last without charging or replacement for a substantial time period. In some embodiments, a communications protocol may be configured to execute data transfer at high speed. In some embodiments, multiple communications sessions may be executed to help ensure data transmission reliability.

In some embodiments, the measurement device includes chemical testing properties to enable chemical testing of a measured liquid or substance, which is initially read off/onto the strip as an analog representation of the test results. Measurement device further includes an analog to digital (A/D) converter to convert the results into a digital format. Measurement device further includes a data processor and data codifier, for generating an optics communication protocol for transmitting the results data in optical form to the smart device. For example, the communications protocol may be based on a Morse code like foundation, by sending long and short flashes of the LEDs to represent bits and bites of the results to be transmitted. Moreover, data transmission confirmations may also be transmitted between the devices, using flashes of the LEDs on the measurement device towards the smart device camera, and flashes of the smart phone screen LEDs/pixels toward the measurement device camera or light sensor.

FIGS. 9A-9B are graphical illustrations of components of an optical communications enabled fluids testing dongle 910 for measuring a sample from a test strip, in optical association with a mobile communications or computing device, according to some embodiments.

FIG. 10 is a flow chart showing a process for fluids testing using a fluids testing dongle optically connected to a mobile communications or computing device, according to some embodiments of the present invention. As can be seen, at step 1005, application software is installed on a smart device. At step 1010 the smart device is paired with a measurement dongle (MD). At step 1015 the MD is coupled to the smart device. At step 1025 one or more elements of the physical coupling wakes up the MD, from deep sleep mode. For example, the disengagement of the MD from an MD holder device, the opening or closing of the clip or spring mechanism, or the coming into proximity with the smart device, etc. Waking up of MD may also wake up the application software on MD, and/or reset the application software to be ready to record a new measurement. At step 1025 a substance or liquid sample is loaded onto a sensor or strip, which is subsequently loaded onto or into MD, for example via a slot for a testing strip. At step 1030 the MD records a measurement on the inserted sensor, and produces a measurement metric, typically in an analog format, representing the physical or chemical measurement. The MD subsequently concerts the analog data to digital data, and thereafter generates an optical signal representing the data to be transmitted. At step 1035 the results are transmitted to the camera of the smart device, which has been set to video capture mode, via an optical signal produced by the array of LEDs on the MD. At step 1040 the data transmittal is confirmed or verified, optionally using an optical signal produced by the screen of the smart device, to be received by a light sensor on the MD. At step 1045 the results received to the smart device are processed and displayed on the application software. At step 1050, after successful transmission of results has been confirmed, and end session signal may be transmitted from screen of smart device to MD light sensor, thereby ending the session and putting the MD power source into sleep mode, to minimize power usage on MD.

In accordance with some embodiments of the present invention, a method for bi-directional communications is provide, using an optical communications protocol or method, using flashes of LEDs to transmit data between a sensor or measurement dongle and smart device equipped with a camera and a screen.

FIG. 11 is a table showing an example of an algorithm using RGB light to provide signals to a device camera, for enabling fluids testing using a fluids testing dongle wirelessly connected to a mobile communications or computing device, according to some embodiments of the present invention. As can be seen, using RGB light to signal to a computing device camera (without intensity control), there are 8 different colors, although other configurations may be used. By using a photo-sensor on the screen to get ACK and NCK, can be modified to transmit/receive more signals.

As can been in FIG. 11, a table for coding is provided showing an example of light signals generated by different color diodes to represent data to be transmitted. In the example provided 8 colors may be used to provide a digital language for communicating using optical signals. In one example, light chromaticity can be translated into binary code, and binary code can be translated into any selected output. In the table shown in FIG. 11, when value is 0, LED is off, and when value is 1, LED is on). Further, in accordance with the color outcome from the combination of the respective LEDs, based on a selected code for each color, a communications protocol or language is generated.

In a further example, more colors may be created, thereby allowing for longer code, in accordance with the intensity of each LED, not just the on and off value (e.g., similar to a screen showing color from a RGB basic colors selection). Further, the speed of data transfer may be able to reach the theoretical speed "Nyquist rate" i.e. if the frame rate of the camera is 30 fps (frame per second) we can reach 15 Hz i.e. 15 colors a second. In still further implementations, areas of color in a frame may be analyzed to enhance code.

Figure 12:
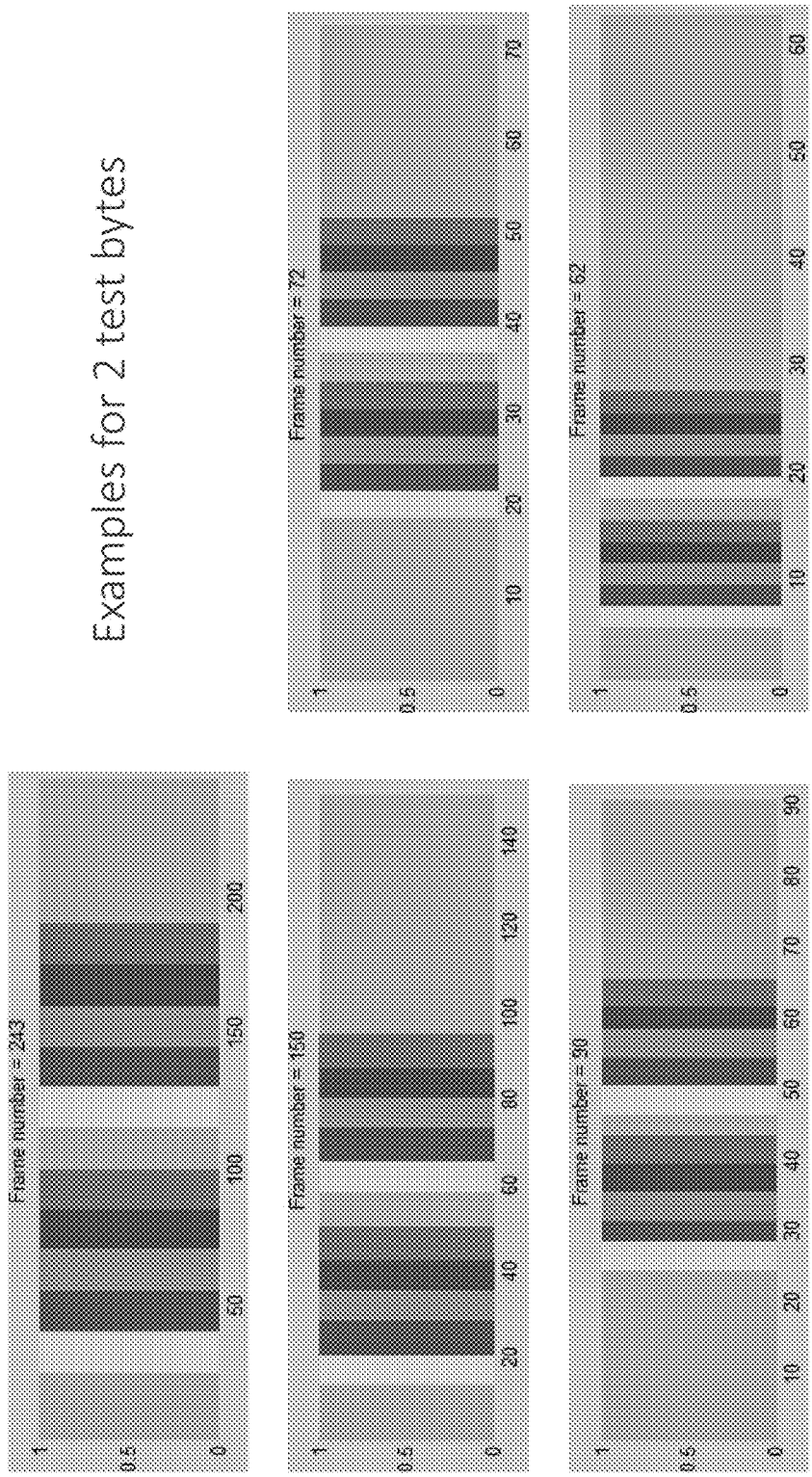
FIG. 12 is a collection of screen shots showing examples of 2 test bytes transmitted at different frequencies, to provide signals based on RGB light to a device camera, for enabling fluids testing using a fluids testing device wirelessly connected to a mobile communications or computing device, according to some embodiments of the present invention.

FIG. 12 is a collection of screen shots showing examples of 2 test bytes transmitted at different frequencies, to provide signals based on RGB light to a smart device camera, for enabling fluids testing using a fluids testing device wirelessly connected to a mobile communications or computing device, according to some embodiments of the present invention. As can be seen the changes in frame rates of the video scream received by the smart device may powerfully impact on the amount of data to be received by the smart device. In one example, as can be seen, at 15 Hz frame rate, between 60 and 250 frames per second may be received.

In one embodiment as described in FIG. 12, the X-axis represents the frame number, starting from the upper left to the lower right graph, the first picture starts at 30 and ends at around 190, for a total of ~160 frames. The number of frames is thereafter reduced in each graph until substantially the same information is embodied in ~22 frames (Nyquist rate), at which stage the theoretical rate may be reached.

Figure 13:
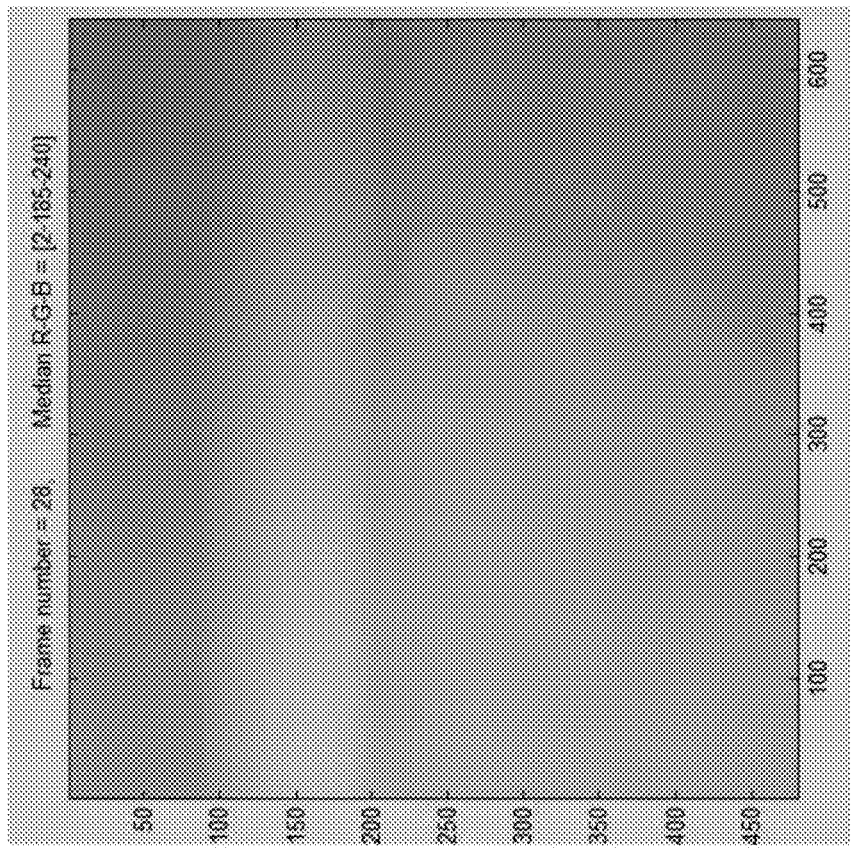
FIG. 13 is a screen shot of a chart of color outputs reflecting a signal analysis for enabling fluids testing using a fluids testing device wirelessly connected to a mobile communications or computing device, according to some embodiments of the present invention.

FIG. 13 is a screen shot of a chart of color outputs reflecting a signal analysis for enabling fluids testing using a fluids testing dongle wirelessly connected to a mobile communications or computing device, according to some embodiments of the present invention. As can be seen in the FIG., the color change is shown in a signal frame, and this information may be used to improve the speed of data transmission, by dividing each frame to a selected area. In one example, when using 15 Hz the full S/N may be transmitted in less than 3 seconds.

In accordance with some embodiments, the MD power source may be powered using the smart device flash, using energy harvesting.

In accordance with some embodiments, a line may be generated on the screen of the smart device, to show the user an indication for optimal placement of the MD, in accordance with the dimensions of the user's smart device. Further, the smart device and/or MD may give the user feedback or guidance as to where to place or position the MD.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A system for enabling optical transmission of data between a sensor and a smart device, comprising:
   a computing device configured to run testing related code of a materials testing Application, wherein the computing device has a screen and a camera in proximity to the screen;
   a materials testing dongle including a light source and a light receiver, wherein the testing dongle is adapted to be placed at least partially over the computing device screen, and at least partially over the computing device camera;
   wherein the computing device is configured to communicate material testing data optically to the testing dongle using at least a part of the computing device screen, and the testing dongle is configured to communicate data optically to the computing device using the light source; and
   wherein the computing device is configured to receive material testing data optically from the testing dongle using the camera, and the testing dongle is configured to receive data optically from the computing device using the light receiver.

2. The system of claim 1, wherein the testing dongle is configured to be attachable to a testing apparatus, wherein when attached thereto, the power source for the testing dongle is passive, whereas when the testing dongle is detached from the testing apparatus, the power source for the testing dongle is in sleep mode.

3. A method for fluid measurement testing using a communications adaptor device, for enabling optical communications between a measurement device and a smart device having a screen and a camera and having application software installed therein, the method comprising:
    pairing a measurement dongle, the dongle having one or more LEDS, with the smart device;
    loading a substance for testing onto a sensor or strip/stick;
    loading the sensor or strip/stick onto or into the measurement dongle;
    recording a test measurement on the measurement dongle, from the substance on the inserted strip/stick;
    producing a test measurement signal;
    generating an optical signal representing data from the test measurement;
    transmitting the test measurement data to the camera of the smart device, which uses video capture to record optical signals produced by the one or more LEDs on the measurement dongle;
    verifying the data transmittal, using an optical signal produced by the screen of the smart device, and received by a light sensor on the measurement dongle that is at least partially covering said screen; and
    processing and displaying the test measurement data received by the smart device.

4. The method of claim 3, further comprising using flashes of the one or more LEDs to transmit said test measurement data.

5. The method of claim 3, further comprising one or more steps selected from the steps including:
    waking up the measurement dongle from sleep mode via one of (a) disengaging the measurement dongle from a measurement dongle holder; (b) opening or closing a clip or spring mechanism; and (c) bringing the measurement device into proximity with the smart device.

* * * * *